United States Patent
Boheim et al.

[11] Patent Number: 5,891,169
[45] Date of Patent: Apr. 6, 1999

[54] METHOD OF PROCESSING SIGNALS CHARACTERISTIC OF CARDIAC ACTIVITY AND AN ASSOCIATED DEVICE

[75] Inventors: Gustav Boheim; Paul Wyborny; Dennis Digby; Tran Thong, all of Lake Oswego, Oreg.; Max Schaldach, Erlangen, Germany

[73] Assignee: Biotronik Mess- und Therapiegeraete GmbH, Berlin, Germany

[21] Appl. No.: 776,294

[22] PCT Filed: Jul. 28, 1995

[86] PCT No.: PCT/DE95/01030

§ 371 Date: Jan. 29, 1997

§ 102(e) Date: Jan. 29, 1997

[87] PCT Pub. No.: WO96/04042

PCT Pub. Date: Feb. 15, 1996

[30] Foreign Application Priority Data

Jul. 30, 1994 [DE] Germany ............... 44 27 845.4

[51] Int. Cl.[6] ............................................. A61N 1/39
[52] U.S. Cl. ................................................... 607/4
[58] Field of Search ........................... 607/23, 9, 4–6; 600/517, 518

[56] References Cited

U.S. PATENT DOCUMENTS

| | | | |
|---|---|---|---|
| 3,605,727 | 9/1971 | Zenevich et al. | 600/517 |
| 3,646,930 | 3/1972 | Patterson et al. | 600/517 |
| 4,023,564 | 5/1977 | Valiquette et al. | 600/517 |
| 4,184,493 | 1/1980 | Langer et al. | |
| 4,393,877 | 7/1983 | Imran et al. | 600/518 |
| 4,523,595 | 6/1985 | Zibell . | |
| 5,439,483 | 8/1995 | Duong-Van | 600/518 |
| 5,470,342 | 11/1995 | Mann et al. | 607/4 |

FOREIGN PATENT DOCUMENTS

| | | |
|---|---|---|
| 0349130 | 1/1990 | European Pat. Off. . |
| 0398488 | 11/1990 | European Pat. Off. . |
| 0402508 | 12/1990 | European Pat. Off. . |
| 0607637 | 7/1994 | European Pat. Off. . |
| 3739014 | 5/1988 | Germany . |

*Primary Examiner*—William E. Kamm
*Assistant Examiner*—Kennedy J. Schaetzle
*Attorney, Agent, or Firm*—Spencer & Frank

[57] ABSTRACT

A method for processing a signal characteristic of cardiac activity in the atrium (A) and/or ventricle (V) of a heart (H) and for evaluating this signal with a view to obtaining a control signal for a cardiac pacemaker and/or defibrillator (3) can be carried out by: receiving a time dependent signal from at least one intracardial signal sensor (1, 2) in the atrium and/or ventricle; feeding the signal picked up by each signal sensor (1, 2) to a read and evaluation circuit (6) with a threshold characteristic; comparing the signals with a detection threshold; evaluating the result of the comparison to obtain an indication as to the presence of normal sinus-type cardiac activity or fibrillations; and producing the control signal, which characterizes the comparison result. The signal from the at least one sensor (1, 2) is fed to a first input stage (8, 11) which has a first adjustable detection threshold (TS(A), TS(V)) that is constant in time and to a second input stage (9, 10) which has a second adjustable detection threshold TL(A), TL(V) that can be adjusted independently of the first detection threshold but is constant in time once set. The signal from the at least one intracardial signal sensor is processed in these first and second input stages.

31 Claims, 4 Drawing Sheets

METHOD OF PROCESSING SIGNALS CHARACTERISTIC OF CARDIAC ACTIVITY AND AN ASSOCIATED DEVICE

BACKGROUND OF THE INVENTION

The invention relates to a method for receiving signals characteristic of cardiac activities in the atrium and/or ventricle of a heart and for evaluating the signals to obtain a control signal for a heart pacemaker and/or defibrillator. The invention also relates to a device for performing the method.

Implantable heart pacemakers and defibrillators have an input stage connected to an intracardial electrode for receiving and amplifying intracardially picked-up cardiac activity potentials and an evaluation unit for evaluating them and deriving control signals for operating the pacemaker or defibrillator. If signals from the heart chamber (ventricle) as well as the atrial area (atrium) are required for the control, then one electrode is provided for each, and the input stages (if necessary also components of the evaluation unit) generally form separate channels, for which the processing characteristics (sensitivity or detection threshold, filtering and amplification parameters) can be adjusted separately.

With automatic defibrillators and double-function pacemakers, which function as defibrillators if necessary, the initial stages must also detect and preprocess as signals the cardiac action potentials or signals that appear with normal cardiac action (sinus rhythm), such as occur with the various arrhythmic conditions of the heart.

The signal amplitudes for the intracardially picked-up signals, which characterize the different heart rhythm conditions, differ considerably from each other, as can be seen in FIG. 2. Graph I here illustrates a typical sinus rhythm with normal heart function, Graph II the electrogram for a ventricular tachycardia and Graph III that of a heart chamber fibrillation (ventricular fibrillation). A suitable detection threshold TI, TII, TIII is respectively marked here with a dashed line (Graph I), a dash-dot line (Graph II) or a double dash-dot line (Graph III).

An embodiment of the initial stage of a pacemaker with an automatic gain control (AGC) is known—for example from EP 0 349 130 A1. It is designed to improve the signal/noise ratio when operating jointly with a band-pass filtering.

Furthermore, it is known from U.S. Pat. No. 4,184,493 A1 to provide an automatic gain control with an automatic, implantable defibrillator. Together with a high-pass filtering, this causes a far-reaching suppression of S and T components of the electrogram and thus prevents a possible faulty interpretation of a "normal" electrogram as ventricular fibrillations, based on the detection of these signal components.

In an implantable cardioverter/pacemaker according to DE 37 39 014 A1, the AGC can be used further in connection with the detection of signal components with low amplitude and thus a ventricular fibrillation.

Such a function of the AGC is illustrated in FIG. 3, where the drawn-out graph represents an electrogram where a sinus rhythm can be seen in the left segment (range A), a ventricular tachycardia in the center segment (range B) and ventricular fibrillations in the right segment (range C). The upper, dashed line represents the effective detection threshold as it is adjusted by the AGC, and the events demonstrated for the illustrated, time-dependent course of the detection threshold are shown in the lower section of the Figure.

Certain appearances of ventricular fibrillation are characterized in the intracardial electrogram by the occurrence of a relatively low-frequency signal pattern with comparably high amplitude, superimposed on the fibrillation signals with considerably higher frequency and weaker fibrillation signals; compare in this case perhaps U.S. Pat. No. 4,523,595, especially FIGS. E12 and E13. Such an electrogram is shown (diagrammatically) in FIG. 4, for which the layout is analogous to FIG. 3. As is illustrated with this Figure, with the relatively slow rise of the amplification and the correspondingly slow decline of the detection threshold after each signal of the superimposed signal pattern that respectively increases the threshold, the AGC prevents a detection of the signals that characterize the fibrillation. As a result of this, the defibrillator cannot become operational, even though it may be needed.

With an automatic defibrillator, the automatic gain control (AGC) therefore can possibly result in grave operational defects—not to mention the fact that its realization for strongly differentiated signal images in the form of cardiac electrograms is not simple and is rather costly.

SUMMARY OF THE INVENTION

It is therefore the object of the invention to present a method and a device of the aforementioned type, which permit a reliable detection and differentiation of various cardiac conditions on the basis of an intracardial electrogram with justifiable expenditure, as well as an automatic defibrillator that uses this method or this device.

The solution to this object includes the idea of undertaking a signal processing of intracardially picked-up heart signals by using two different, permanently effective detection thresholds that do not change during the measuring, one of which is tailored exclusively to the detection of fibrillation signals. This eliminates an unavoidable danger in the automatic gain control of "overlooking" signals with small amplitudes, which indicate a ventricular fibrillation, with the simultaneous appearance of signals with considerably larger amplitude, and the design for the detection circuit can be simplified at the same time owing to the elimination of the involved AGC.

The signals on which this is based can be picked-up in particular by using at least one intracardially arranged sensing electrode—wherein they represent the time-dependent course of a cardiac activity potential at the sensing location—or if necessary with one or several intracardially arranged pressure transducers—wherein an electric signal spectrum exists that reflects intracardially time-dependent pressure fluctuations. However, other sensors can be used as well, which basically can supply signals indicating the appearance of fibrillation events.

The various detection thresholds are realized respectively in a separate input stage with a design that is known per se, wherein the signal spectrum received in dependance on the time is subjected to an evaluation with the threshold value comparison result in order to gain a statement with respect to the occurrence of sinus-type cardiac activities or ventricular fibrillations, and finally a control signal is generated that characterizes the evaluation result, which in particular can serve to control a pacemaker and/or stand-by defibrillator.

The processing method with the low detection threshold advisably comprises a preprocessing step with (wide-band) gain and a high gain factor, wherein cutting the signal components off above a predetermined limit that is selected above the level of the lower detection threshold—in particular also of stimulus pulse artefacts—improves the transfer characteristics for the weak fibrillation signals. Another improvement with respect to this can be achieved by blanking out the signal components during a predetermined time interval, following the appearance of a signal component located above the predetermined limit.

The pre-processing step advantageously includes digitizing, at least in the signal path with the low threshold, wherein the digitizing takes place after signal components with higher amplitude are cut off, if such is planned. This permits in a cost-effective way the use of an A/D converter with low accuracy or processing width and subsequently the use of a digital comparator for the threshold value discrimination and a simple digital analysis in a microprocessor or an integrated evaluation circuit. Furthermore, it permits in a simple way the temporary storage of the signals for a later, different analysis. The adjustment of the lower detection threshold can be made favorably during an initial measuring, depending on the result of an analysis of the maximum or an average amplitude or the signal energy for that component of the total signal spectrum, which is not cut off.

In order to be able to distinguish the weak fibrillation signals with sufficient certainty from the noise and thus prevent possibly dangerous false alarms of a defibrillator, it is useful to distinguish between the signals fed to the second input stage or preprocessed there and the noise, based on an amplitude and/or frequency discrimination. It is useful to do this with the aid of digitized signals. In case of an amplitude discrimination, a limit is preset, for which the signals located above are classified as significant and signals located below are classified as noise. The (low) threshold is then set, for example, to 75% of the peak level of the signals classified as significant.

The evaluation interval can also have a timed averaging with respect to the detection signal train for a preset number of signals, preprocessed with the low threshold, or a predetermined time cycle for noise suppression and the determination of an average rate for these signals, wherein a signal is output that characterizes the existence or non-existence of fibrillations, depending on the average rate.

Furthermore, it is possible to determine the signal peak values or a signal mean value or the average signal output or the root-mean-square value of the signal amplitude for the signals above the second detection threshold and to output a signal that characterizes the existence or non-existence of fibrillations depending on the average rate and the signal peak value, the signal average value or the root-mean-square value. This presupposes the existence of typical or comparative signal images, which the cardiologist generally is familiar with or which can be determined—patient specific—for example with provoked fibrillations.

For one particularly advantageous use of the two-threshold principle according to the invention, the evaluation includes a timed message with respect to the detection signal train obtained with the higher threshold attuned to the signals stemming from sinus-type cardiac events, via a predetermined number of signals or a predetermined time cycle for determining an average rate for these signals, that a time window is determined from the average rate (escape interval, perhaps specific for bradycardia), and that a signal is issued within the time window that characterizes the type of actual cardiac activity (maybe also a bradycardia), depending on the appearance or non-appearance of signal components located above the first detection threshold as well as located above the second detection threshold.

With the inventive device, a separate evaluation unit with a control signal output for issuing a control signal characterizing the respective evaluation results can be coordinated with each input stage. However, it is also possible to have a joint or linked evaluation in sections—for example within the meaning of the previous paragraph.

The input stage with the low threshold can have in particular a wide-band amplifier with a high amplification factor. For advantageous embodiments—corresponding to advantageous embodiments of the measuring method—it can also have a level limiter circuit for cutting off signal components located above a predetermined limit that is selected above the level for the second detection threshold and, if necessary, a scanning or blanking circuit for blanking out the signal components during a predetermined time interval, following the appearance of a signal component above the predetermined limit.

Furthermore, it is advisable to have an A/D converter for digitizing the picked-up or already preprocessed signals. In that case, the comparator unit for threshold value discrimination can be configured as digital comparator. If a level limiter circuit exists, the input for the A/D converter is connected to the output for the level limiter circuit and the A/D converter can be a model with relatively low processing range. A signal memory can also be provided, for which the data input can be connected to the A/D converter output and its data output with an internal or external evaluation unit.

Timing means (timers) can be assigned to the first and second input stage for determining evaluation time intervals, and they respectively have a rate determination circuit for determining an average rate for the signal components located above the respective detection threshold. Alternatively or additionally, means can be provided during a preceding measuring cycle for the amplitude discrimination and, if necessary, amplitude mean value formation as well as means for adjusting the second detection threshold, depending on the result of an evaluation of the maximum or an average amplitude of the total signal spectrum component that is not cut off.

The means for amplitude discrimination are—if a digital signal processing takes place—usefully connected in series after the A/D converter.

The inventive device can be used with an automatic defibrillator, specifically also one that additionally functions as a demand pacemaker.

DESCRIPTION OF THE PREFERRED EMBODIMENTS

Figure 1:
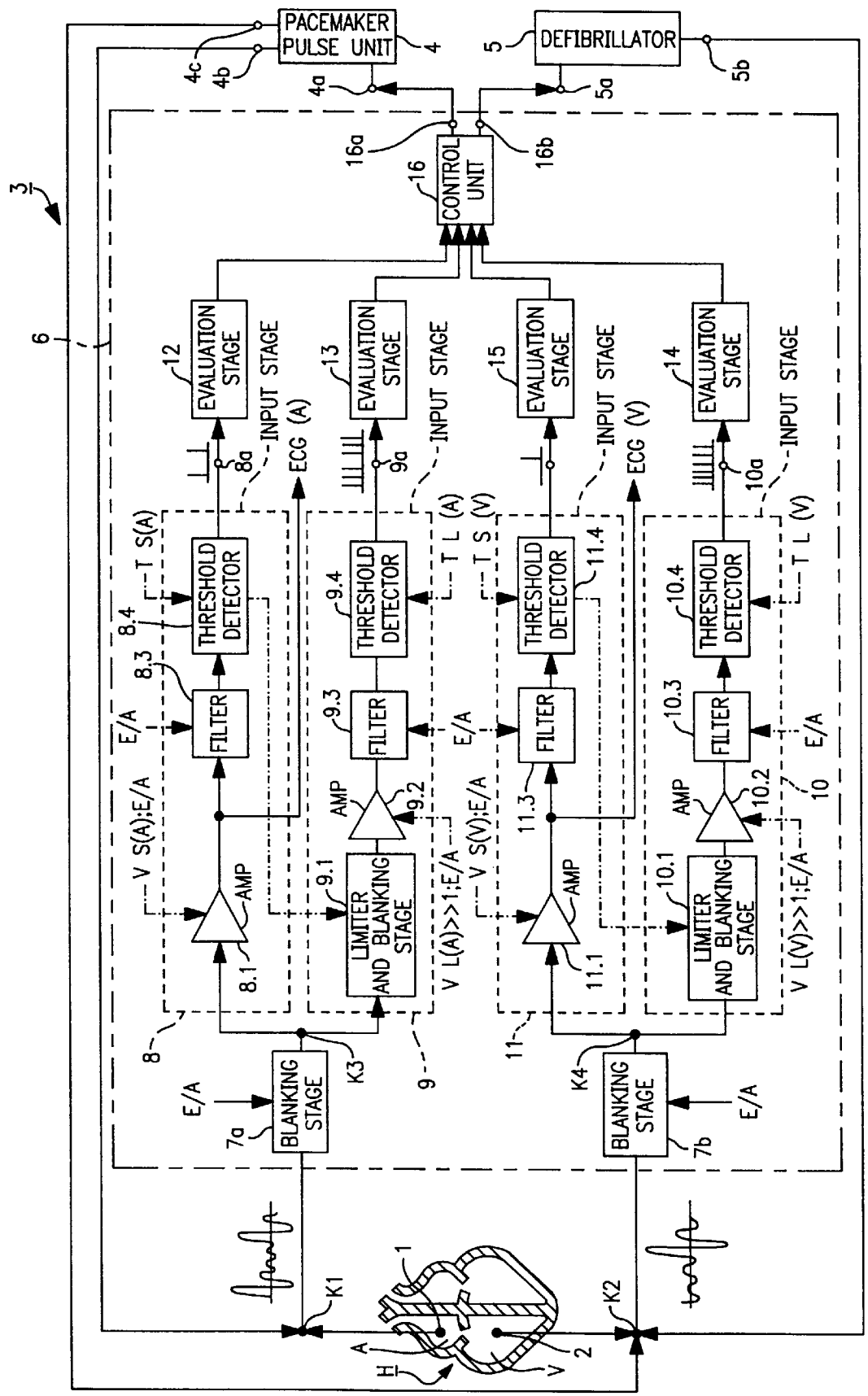
FIG. 1 is a very simplified block diagram of a two-chamber demand pacemaker with standby defibrillator for which one embodiment of the invention is realized.
Figure 2:
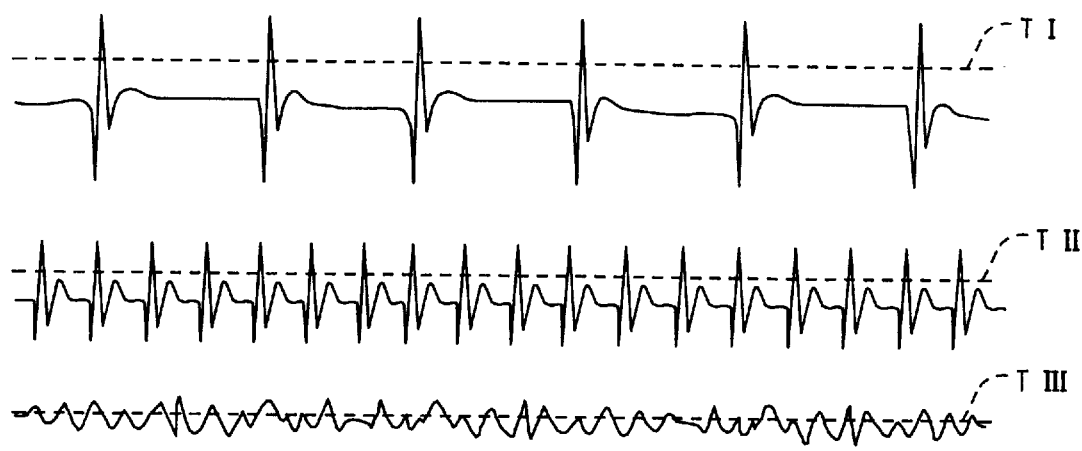
FIG. 2 is a representation of intracardially picked-up electrograms (ECG signals) of various cardiac activities.
Figure 3:
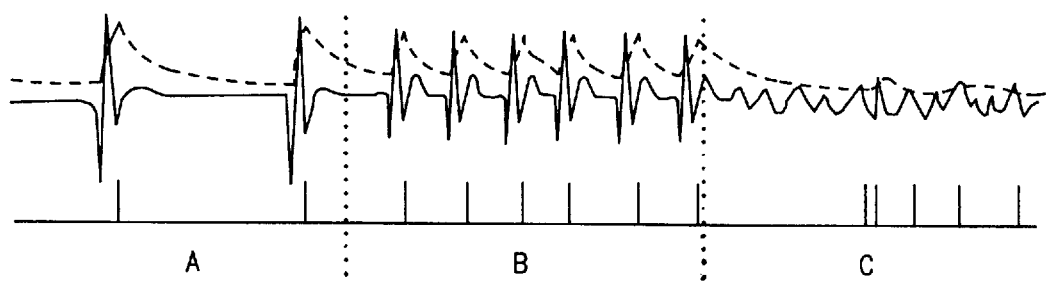
FIG. 3 is a diagrammatic representation of an electrogram of various chronologically successive cardiac activities characterizing the course for the detection threshold and the detected signals for a detection method based on the Prior Art (with AGC)

FIG. 1 is a very simplified representation—in particular by omitting the components for a power supply, programming, etc.—of a twin-chamber pacemaker 3 connected with electrodes 1 in the atrium A and 2 in the ventricle V of a heart H, having a pacemaker pulse unit 4 and an integrated defibrillator discharge stage 5.

The pacemaker pulse unit 4 has a control input 4a and two separate pulse outputs 4b and 4c for atrial or ventricular stimulation pulses. The output 4b is connected via a node K1 with the atrial electrode 1 and the output 4c via a node K2 with the ventricular electrode 2. The defibrillator discharge stage 5 has a control input 5a and a pulse output 5b for cardiac stimulation pulses, which is also connected via the node K2 to the ventricular electrode 2. (In its function as a defibrillation electrode, the electrode 2 here is shown only diagrammatically; additional intracardial or subcutaneous electrodes can also be provided for the cardiac stimulation)

In addition to is functioning as stimulating electrodes, the electrodes 2 and 3 function also as signal sensors for atrial or ventricular recorded electrograms (intracardial ECG signals). That is why they are connected via the nodes K1 or K2 with a read and evaluation circuit 6 of the pacemaker/defibrillator 3. Their output signals travel via scanning or "blanking" stages 7a and 7b that can be switched on and off (maybe triggered directly by transmitted stimulation or defibrillation pulses) as protection against overload through stimulating pulses to nodes K3 or K4, where the signal path for the atrial and ventricular signal respectively branches off.

From node K3, the atrial signal is fed to two separate input stages 8 and 9, and the ventricular signal is fed from node K4 to two separate input stages 10 and 11.

The continued signal path for both signals is in principle the same—except for specific adjustments of the modules—so that in the following only the signal path for the signal obtained in the atrium is described. For input stages 10 and 11, the modules with analogous numbering correspond to the individual modules for inputs stages 8 and 9, that is the modules 10.1 and 11.1 corespond to modules 9.1 and 8.1.

The first input stage 8 for the atrial signal has a read amplifier 8.1, which can be switched on and off through corresponding control signals referred to as "E/A" or "VS (A)" with adjustable amplification, and the input stage 9 has a read amplifier 9.2. The latter has a wide-band design, can also be switched off selectively via a signal "E/A" and has a relatively high amplification factor that can be adjusted via a control signal ("VL(A)").

Within the first input stage 8, the amplified signal from the read amplifier 8.1 travels to a filtering stage 8.3—which can also be switched on/off via a signal "E/A"—and from there to a threshold value detector circuit 8.4 with a detection threshold that can be adjusted via a control signal "TS(A)," which lies within the standard detection threshold range for pacemaker input circuits for sinus-type cardiac event (without AGC). In addition, a tapping point for an unfiltered intracardial ECG signal "ECG(A)" is provided between the read amplifier 8.1 and the filtering stage 8.3.

Within the second input stage 9, the input signal initially travels to an integrated level limiter stage and scanning or blanking circuit 9.1, which can be activated via a control signal from the threshold value detector circuit 8.4 of the first input stage 8 and which prevents overloads in this signal path. From the output of this stage it travels to the read amplifier 9.2 and from there as wide-band amplified signal to a filtering stage 9.3, which also can be switched on/off via a signal "E/A." From there, it finally arrives at a threshold value detector circuit 9.4 with a detector threshold that can be adjusted via a control signal "TL(A)," which is located below the threshold for the first threshold value detector circuit 8.4 and the standard detector thresholds of pacemaker input circuits (without AGC).

The modules 8.1, 8.3 and 8.4 form the first input circuit and the modules 9.1, 9.2 9.3 and 9.4 from the second input circuit for the atrial measuring signal.

In the threshold value detector stages 8.4 or 9.4 and based on the detector threshold adjustment, the input signal is respectively converted as known per se into a train of individual pulses. The pulse trains are initially fed via the signal outputs 8a or 9a to separate evaluation stages 12 or 13, where they are used for classifying or identifying the cardiac events detected through the atrial measurement.

The ventricular signals, which are processed in the stages 10.1 to 10.4 or 11.1 to 11.4 analogous to the above description, are analyzed in a similar way in evaluation stages 14 or 15, and all evaluation or intermediate data are subsequently fed to a central processing and control unit 16, which finally readies at the output 16a and 16b control signals for operating the pacemaker pulse unit 4 or the defibrillator stage 5.

Figure 5:
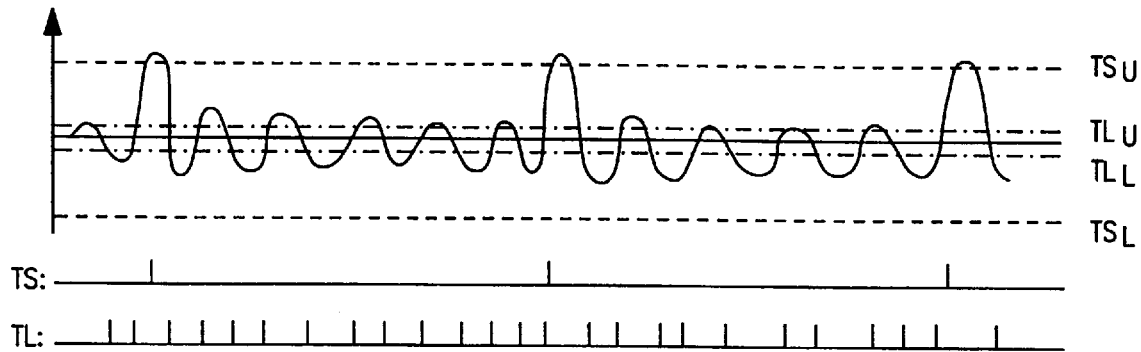
FIG. 5 is a diagrammatic representation of the electrogram according to FIG. 4 characterizing the chronological course of the detection thresholds and the respective detected signals for a detection method based on one embodiment of the invention.

The operation of the arrangement shown in FIG. 1 is explained by referring to FIG. 5, which is a diagrammatic representation of an (atrial or ventricular) recorded electrogram by characterizing the course in time of the detection thresholds of the two input stages 8 and 9 or 10 and 11, which are assigned to the electrodes 1 or 2, as well as providing their output signal trains.

Deviating from the adjustments normally made in practical operations, the simplifying assumption is made in FIG. 5 that both read amplifiers have the same amplification factor and that no level cut-off, scanning or varied filtering occurred in both signal paths. In that case, the same signal spectrum is present at the input for threshold value detectors 8.4 and 9.4 (or 10.4 and 11.4). The discrimination of the detection thresholds $TS_U$, $TS_L$ and $TL_U$, $TL_L$ results in the detection signal trains "TS" or "TL," which are indicated in the lower section of the Figure—with the same time scale as in the upper section.

Figure 4:
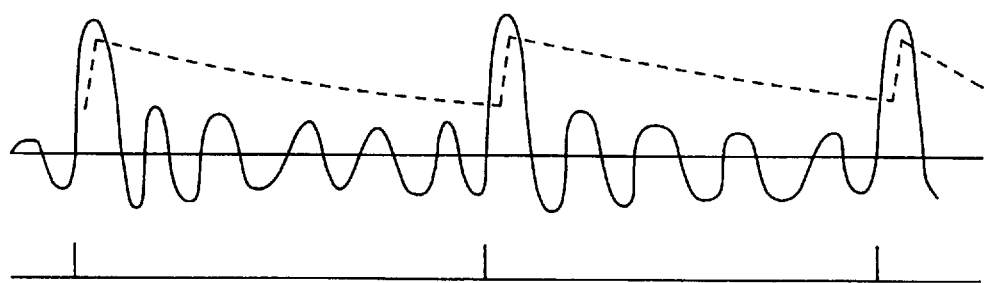
FIG. 4 is a diagrammatic representation of a special electrogram characterizing the chronological course of the detection threshold and the detected signals for a detection method based on the Prior Art (with AGC)

A comparison with FIG. 4, which is explained at the beginning of the description and shows the same electrogram, illustrates the gain achieved through the use of two detection thresholds with constant time:

While it is not possible with the standard method for processing the inputs signals in an input stage with AGC to detect the signal components which are located below the larger signals and indicate a cardiac fibrillation, this is easily possible by means of the above-described device. In addition, it is possible—and this is not the case when using only one, low threshold—to have a pre-classification of the signals, which in the electrogram shown is a separation between the fibrillation signals and the signals indicating a superimposed, regular cardiac activity. This permits an exact analysis of the heart condition in the following evaluation stages and the correct control of the pacemaker or the defibrillator.

The use of level limiters and scanning circuits 9.1 and 10.1 further improves the transmission behavior in the signal paths with the low detection threshold. While input signals with high level exceed the standard detection threshold of input stage 8, their activation permits a high amplification in the input stage 9, which equals a low effective threshold. This can be used in such a way that the detector threshold adjusted in the threshold value detector 9.4, can be in the normal range, while the input stage 9 still has a low, effective detection threshold.

Figure 6:
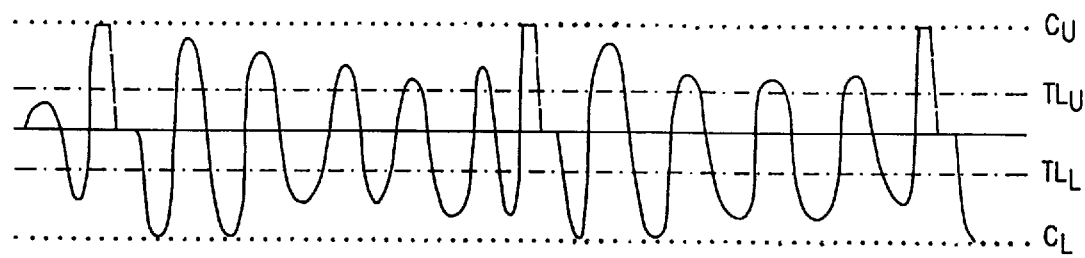
FIG. 6 is a diagrammatic representation of the electrogram according to FIGS. 4 and 5 with higher amplification, peak cut-off and scanning of signal components for a detection method according to another embodiment of the invention.

An electrogram processed with level limiting and scanning corresponding to FIGS. 4 and 5 is shown in FIG. 6. The upper and lower detection thresholds $TL_U$ or $TL_L$ correspond to FIG. 5. However, the high amplification assumed in FIG. 6 necessitates another scale for the ordinate as compared to FIG. 5. The electrogram ranges where a level limiting to a preset level value C" has started are shown. The Figure shows that one each scanning range follows.

The level limiting otherwise facilitates a digitizing and continued digital processing of the signals, since this reduces the number of required quantization stages and the processing width. In particular, the threshold value detection stages then can have digital comparators, and the evaluations can take place in a microprocessor configuration.

Figure 7:
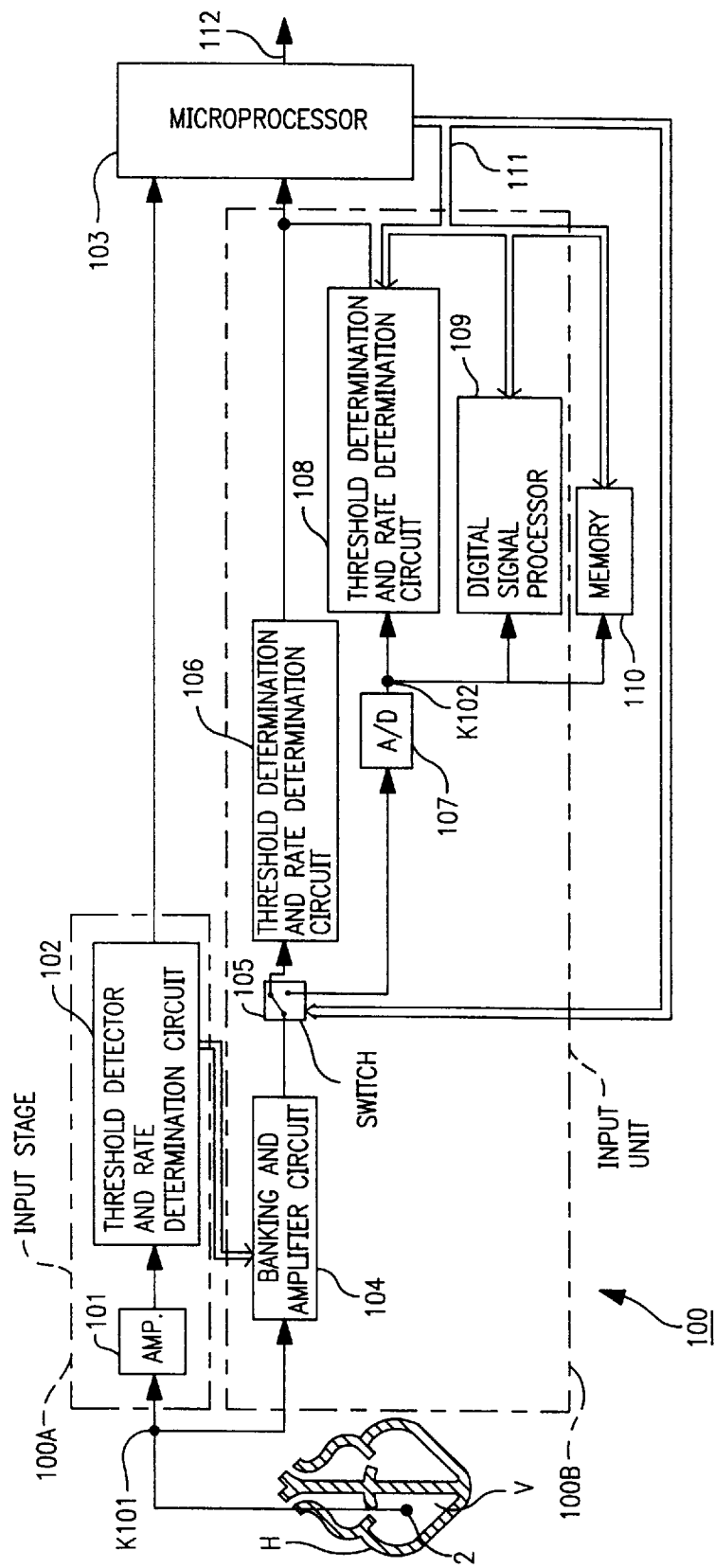
FIG. 7 is a very simplified block diagram of a read circuit based on an embodiment of the invention.

A corresponding read and evaluation circuit 100 as an additional embodiment of the inventive device is shown diagrammatically in FIG. 7.

A cardiac activity potential picked-up via a sensing electrode 2 in the ventricle V of a heart H travels via a node K101 on the one hand to a traditional read amplifier 101 and from there to a first integrated threshold value detector and rate determination circuit 102, from which output signals gained following the threshold value discrimination and a rate determination of the signal components with high amplitude are transmitted to a microprocessor 103.

On the other hand, the input signal travels to an integrated blanking and wide-band amplifier circuit 104 with high amplification, for which the blanking behavior is controlled from the stage 102.

The amplified signal will be transmitted by a switching unit 105 selectively to a threshold value detector (analog) and rate determination circuit 106, from which output signals gained as a result of the threshold value discrimination and a rate determination of the signal components with small amplitude are transmitted to the microprocessor 103, or are initially fed to an A/D converter 107.

The output for the A/D converter 107 is connected via a node K102 with the inputs of a digital threshold value detector and rate determination circuit 108, a digital signal processor 109 and a digital ECG memory 110, which are all linked via a bus 111 with the microprocessor 103. In addition, the output for stage 108 is connected to the microprocessor via a standard signal line, through which the results of the digital processing in stage 108 are transferred (alternative to results gained through the analog signal processing in stage 106).

The microprocessor 103 makes signals 112 available for subsequent processing and/or control stages or an output to the outside (perhaps for an external ECG analysis).

The modules 101 and 102 form a first input stage 100A with a standard threshold and the modules 104 to 109 a second input stage 100B with a low threshold.

Insofar as it differs from the one shown in FIG. 1, this circuit operates as follows:

In the first threshold value detector and rate determination stage 102, the signal components with high level are initially measured and their average rate determined. In comparison to stored values, it is possible to initially conclude from this (in cooperation with the microprocessor configuration 103, which also includes a corresponding data memory) that a normal sinus rhythm, a tachycardia or a possible fibrillation are present.

In the second (analog) threshold value detector and rate determination circuit 106, the rate for low-level signals is determined correspondingly—by including an accumulation or taking the mean—and from this (again in cooperation with the microprocessor and a data memory), it can be determined whether fibrillations are present. If such are detected, the result obtained through the high threshold processing is ignored, the result obtained on the path with low threshold is verified by shortening the time interval for taking the mean and—if it is confirmed—a defibrillation is initiated.

Similar steps are taken with the third (digital) threshold value detection and rate determination circuit 108, wherein the signal peaks are possibly evaluated additionally and are consulted for the decision on whether fibrillations are present.

This method of processing makes it also possible in a simple way to verify the existence of a bradycardia in that a time window (bradycardia escape interval) is given, to which all evaluations are applied. If no signal with high amplitude appears during this time window and if the signal peak value for signals with low amplitude is essentially the equal to the average signal level or is below a predetermined limit—which is selected advantageously equal to the low threshold value—then no fibrillations, but only noise are detected. Thus, it is possible to infer the presence of a bradycardia, and the respective pacemaker therapy can be initiated.

With the arrangement according to FIG. 7, several or if necessary all of the microprocessor functions concerning the signal processing can be taken over by a client specific processing circuit.

The adjustment of the low detection threshold for both arrangements according to FIG. 1 or FIG. 7, can be made based on a measurement of the non-limited signal level or the amplitude mean value or the root-mean-square value, wherein signals that may be in the saturation range and certain signal components surrounding the saturated areas must be factored out.

If the threshold itself is adjusted, the amplification factor does not need to be changed, which can be a considerable advantage for digital threshold value processing and a wide-band amplifier with high amplification factor.

In its design, the invention is not limited to the aforementioned, preferred embodiment. Rather, a number of variations are conceivable, which make use of the solution presented, even if it is a totally different embodiment.

What we claim is:

1. A method for processing a signal characteristic of cardiac activities in a chamber of a heart (H) to generate a control signal for at least one of a heart pacemaker and a defibrillator, the signal characteristic of cardiac activities being received from an intracardial signal sensor (1, 2) in the heart comprising the steps of:

(a) feeding the signal characteristic of cardiac activities to a first input stage (8, 11; 100A) with a first, adjustable detection threshold (TS(A), TS(V)), the first detection threshold being constant in time following an adjustment and being set to a signal amplitude for normal sinus-type cardiac activities;

(b) in the first input stage, comparing the signal characteristic of cardiac activities to the first detection threshold and generating a first stage output signal;

(c) feeding the signal characteristic of cardiac activities to a second input stage (9, 10; 100B) with a second detection threshold (TL(A), TL(V)) which is adjustable independent of the first detection threshold, the second detection threshold being constant in time following an adjustment and being set to a signal amplitude for fibrillation events (d) in the second input stage, comparing the signal characteristic of cardiac activities to the second detection threshold and generating a second stage output signal; and (e) evaluating the first and second stage output signals and generating the control signal.

2. A method according to claim 1, wherein the intracardial signal sensor comprises an intracardially arranged electrode (1, 2) which supplies a time-dependent course of a cardiac activity potential as the signal characteristic of cardiac activities.

3. A method according to claim 1, wherein the intracardial signal sensor comprises an intracardially arranged pressure transducer which supplies an electric signal reflecting time-dependent intracardial pressure fluctuations as the signal characteristic of cardiac activities.

4. A method according to claim 1, wherein the second input stage (9, 10; 100B) includes an amplifier with a high amplification factor, and further comprising the step of amplifying the signal characteristic of cardiac activities with the amplifier before step (d) is conducted.

5. A method according to claim 4, wherein step (d) further comprises cutting off components of the signal characteristic of cardiac activity with a magnitude larger than a predetermined limit ($C_u$, $C_L$), the predetermined limit being larger than the level for the second detection threshold ($TL_U$, $TL_L$).

6. A method according to claim 5, wherein step (d) further comprises blanking out of signal components of the signal characteristic of cardiac activities during a predetermined time interval following the appearance of a signal component with a magnitude larger than the predetermined limit.

7. A method according to claim 5, wherein step (d) further comprises digitizing the signal characteristic of cardiac activities after the signal components with a magnitude larger than the predetermined limit have been cut off.

8. A method according to claim 5, further comprising determining, during a preceding measuring cycle, the maximum or average amplitude or the signal energy of a signal component that is not cut off, and adjusting the second detection threshold (TL(A)), (TL(V)) in dependence on the maximum or average amplitude or the signal energy of the signal component that is not cut off.

9. A method according to claim 1, wherein at least one of steps (b) and (d) further comprises digitizing the signal characteristic of cardiac activities, the digitized signal being compared to the respective detection threshold.

10. A method according to claim 9, further comprising identifying noise signals fed to the second input stage (9, 10; 100B) or signals processed in the second input stage on the basis of amplitude discrimination with the aid of the digitized signals.

11. A method according to claim 1, wherein at least one of steps (b) and (d) further comprises storing at least the signal characteristic of cardiac activity or a signal processed in the respective input stage before step (e) is conducted.

12. A method according to claim 1, further comprising identifying noise signals fed to the second input stage (9, 10; 100B) or signals preprocessed in the second input stage on the basis of amplitude discrimination.

13. A method according to claim 1, wherein step (e) comprises finding a time average with respect to a sequence of second stage output signals via a predetermined number of second stage output signals or a predetermined time cycle for determining an average rate for the second stage output signals, a signal characterizing whether fibrillations are present or absent being output depending on the average rate.

14. A method according to claim 13, wherein step (d) comprises determining peak signal values or an average signal value or signal energy of any components of the signal characteristic of cardiac activities that are located above the second detection threshold, and wherein step (e) further comprises outputting a signal characterizing whether fibrillations are present or absent as a function of the average rate and the peak signal values, the average signal value or the signal energy.

15. A method according to claim 1, wherein step (e) comprises determining a time average with respect to a sequence of first stage output signals over a predetermined number of first stage output signals or a predetermined time cycle for determining an average rate for the first stage output signals, determining a time window from the average rate, and outputting a signal characterizing a type of actual cardiac activity in dependence on whether any components of the signal characteristic of cardiac activity are located above the first detection threshold as well as above the second detection threshold during the time window.

16. A device for processing a signal characteristic of cardiac activities in a chamber of a heart to generate a control signal for at least one of a pacemaker and a defibrillator the signal characteristic of cardiac activities being received from an intracardial signal sensor (1, 2), said device comprising:

a first input stage (8, 11) which receives the signal characteristic of cardiac activities, the first input stage having a first detection threshold (TS(A)), TS(V)) that is adjustable but constant in time following an adjustment, the first detection threshold being set to a signal amplitude for normal sinus-type cardiac activities, the first input stage including a comparator unit (8, 4, 11,4) with a first detection output signal (8a, 11a); and a second input stage (9, 10) which receives the signal characteristic of cardiac activities, the second input stage having a second detection threshold (TL(A)), TL(V)) that can be adjusted independent of the first one but that is constant in time following an adjustment, the second detection threshold being set to a signal amplitude for fibrillation events, the second input stage including a comparator unit (9.4, 10.4) with a second detection output signal (9a, 10a).

17. A device according to claim 16, further comprising evaluation unit means (12 to 16) for receiving the first and second detection output signals and generating the control signal in response thereto.

18. A device according to claim 17 in combination with an automatic defibrillator which has a control input (5a) to receive the control signal and which selectively generates a defibrillation pulse if fibrillations occur.

19. A device according to claim 17 in combination with a pacemaker having a control input (4a) to receive the control signal and selectively generating a stimulation pulse if bradycardia appears.

20. A device according to claim 16, wherein the intracardial signal sensor comprises an intracardially arranged electrode (1, 2) which supplies a time-dependent course of a cardiac activity potential as the signal characteristic of cardiac activities.

21. A device according to claim 16, wherein the intracardial signal sensor comprises an intracardially arranged pressure transducer which supplies an electric signal reflecting intracardial, time-dependent pressure fluctuations as the signal characteristic of cardiac activities.

22. A device according to claim 16, wherein the second input stage (9, 10; 100B) further comprises a wide-band amplifier (9.2, 10.2; 104) with a high amplification factor.

23. A device according to claim 22, wherein the second input stage (9, 10; 100B) further comprises a level limiter circuit (9.1, 10.1; 104) for cutting off components of the signal characteristic of cardiac activity with a magnitude larger than a predetermined limit ($C_U$, $C_L$), the predetermined limit being larger than the second detection threshold.

24. A device according to claim 23, wherein the second input stage (9, 10; 100B) further comprises a blanking circuit (9.1, 10.1; 104) for blanking components of the signal characteristic of cardiac activities during a predetermined time interval, following an appearance of a component of the signal characteristic of cardiac activities with a magnitude larger than the predetermined limit.

25. A device according to claim 23, wherein the second input stage further comprises an A/D converter (107) having an input which is connected to an output for the level limiter circuit (104).

26. A device according to claim 23, further comprising means (12 to 16; 103, 109) for amplitude discrimination and means (16; 103) for adjusting the second detection threshold in dependence on an evaluation of the maximum or an average amplitude for a total component of the signal characteristic of cardiac activities that is not cut off during a preceding measuring cycle.

27. A device according to claim 26, wherein the second input stage further comprises an A/D converter, the means for amplitude discrimination (103, 109) being connected in series after the A/D converter (107).

28. A device according to claim 16, wherein the second input stage (100B) further comprises an A/D converter (107) for digitizing the signal characteristic of cardiac activities or signals already preprocessed, and wherein the comparator unit of the second input stage is a digital comparator (103, 109).

29. A device according to claim 28, wherein the device further comprises an evaluation unit (103) which receives the first and second detection output signals and generates the control signal in response thereto, and wherein the second input stage further comprises a signal memory (110) having a data input which is connected to an output of the A/D converter (107), the memory additionally having a data output which is connected to the evaluation unit (103).

30. A device according to claim 16, wherein the device further comprises timing means (103) for determining evaluation time intervals, and wherein each of the first and second input stages (100A, 100B) further comprises a rate determination circuit (102, 104), cooperating with the timing means, for determining an average rate for components of the signal characteristic of cardiac activities that are located above the respective detection threshold.

31. A device according to claim 16, wherein the device further comprises a microprocessor (16; 103) which receives the first and second detection output signals.

* * * * *